United States Patent
Dragan

(10) Patent No.: US 6,261,094 B1
(45) Date of Patent: Jul. 17, 2001

(54) DENTAL CAPSULE FOR PLACEMENT OF ULTRA-HIGH VISCOSITY DENTAL COMPOSITE MATERIAL

(75) Inventor: William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 09/552,338

(22) Filed: Apr. 19, 2000

(51) Int. Cl.⁷ .................................................. A61C 5/04
(52) U.S. Cl. ............................................................. 433/90
(58) Field of Search ........................ 433/90, 89; 222/386; 401/176

(56) References Cited

U.S. PATENT DOCUMENTS

| | | |
|---|---|---|
| 2,903,794 | * 9/1959 | Carfagni ................................. 433/90 |
| 3,521,795 | * 7/1970 | Langhjelm et al. ................... 222/386 |
| 3,581,399 | 6/1971 | Dragan . |
| 3,828,434 | * 8/1974 | Mosch ..................................... 433/90 |
| 4,330,280 | 5/1982 | Dougherty et al. . |
| 4,384,853 | 5/1983 | Welsh . |
| 4,391,590 | 7/1983 | Dougherty . |
| 4,445,626 | * 5/1984 | Steffen et al. ......................... 222/386 |
| 4,767,326 | 8/1988 | Bennett et al. . |
| 4,801,263 | * 1/1989 | Clark ....................................... 433/90 |
| 4,852,772 | * 8/1989 | Ennis, III .............................. 222/386 |
| 4,963,093 | 10/1990 | Dragan . |
| 4,969,816 | 11/1990 | Drumm . |
| 5,083,921 | 1/1992 | Dragan . |
| 5,100,320 | 3/1992 | Martin et al. . |
| 5,129,825 | 7/1992 | Discko, Jr. . |
| 5,165,890 | 11/1992 | Discko, Jr. . |
| 5,172,807 | 12/1992 | Dragan et al. . |
| 5,322,440 | 6/1994 | Steele . |
| 5,421,663 | * 6/1995 | Bravo ................................... 401/176 |
| 5,460,523 | 10/1995 | Schulman . |
| 5,591,027 | * 1/1997 | Muhlbauer ............................. 433/90 |
| 5,707,234 | 1/1998 | Bender . |
| 5,722,830 | * 3/1998 | Brandhorst et al. ................... 433/90 |
| 5,893,714 | * 4/1999 | Arnold et al. ........................... 433/90 |

* cited by examiner

Primary Examiner—Todd E. Manahan
(74) Attorney, Agent, or Firm—Fattibene & Fattibene; Paul A. Fattibene; Authur T. Fattibene

(57) ABSTRACT

This disclosure is directed to a capsule construction for dispensing an ultra dense composite dental restorative material by a syringing technique wherein the capsules include a body portion defining a reservoir having an internal diameter (D) and a connected nozzle angularly disposed relative to the axis of the body portion and having a passageway terminating in a discharge orifice. The nozzle passageway and discharge orifice have an internal diameter (d) so that the ratio of diameters d/D is equal to 1 or slightly less than 1. Bi-directional pistons are provided for extruding the ultra dense material from the capsule. Also, the internal surfaces of the capsules may be coated with lubricating liquid compatible to the ultra dense composite material to be dispensed thereby, and a removable sealing member for sealing the discharge orifice.

17 Claims, 2 Drawing Sheets

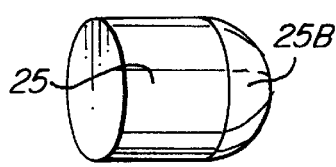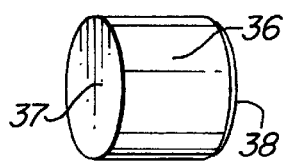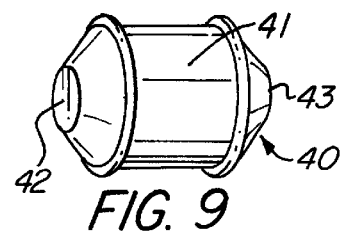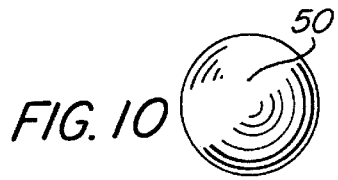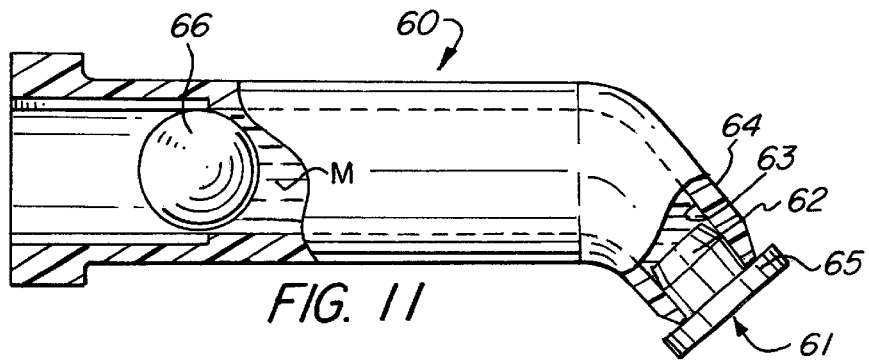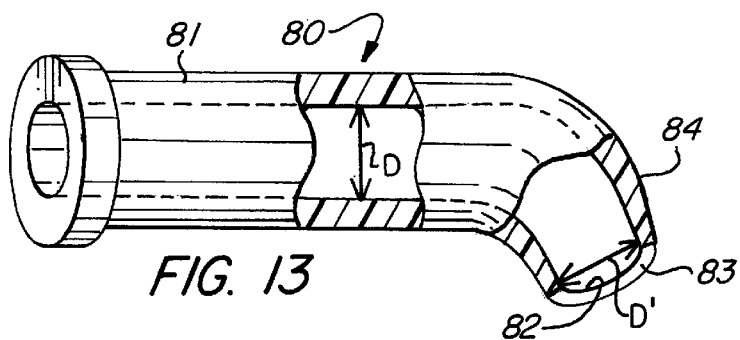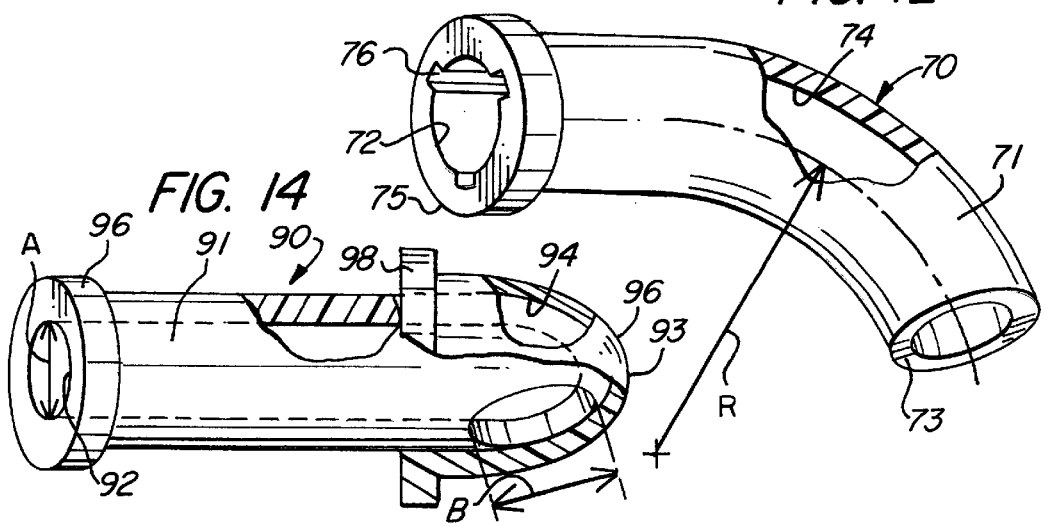

ered composites are rendered "packable" or "condensable" to imitate amalgam in consistency. Such ultra dense or condensable composite materials are particularly suitable for restoring the back or posterior teeth. The particular condensable properties of such ultra dense composite materials makes it difficult to dispense from bulk syringes. The extreme viscous properties of such ultra dense dental composites have also prohibited the placement of such ultra dense composite material by the use of the syringing technique utilizing the known capsule constructions, which the dental profession has virtually universally adopted as the preferred method of delivering a composite material directly into a prepared cavity.

DENTAL CAPSULE FOR PLACEMENT OF ULTRA-HIGH VISCOSITY DENTAL COMPOSITE MATERIAL

FIELD OF THE INVENTION

This invention is directed generally to a dental capsule for the direct placement of composite type restorative dental material, and more specifically to a unit dose dental capsule for the direct placement of ultrahigh density, i.e. packable or condensable composite materials to a prepared tooth by syringing.

BACKGROUND OF THE INVENTION

Dental composite material for restoring teeth was first introduced into dentistry about the mid 1960's. The initial composites had a paste-like consistency. As a result, dentists encountered considerable difficulty in the placement of such composite material into a prepared tooth. Generally, the dentist would apply such paste-like composite resin material to a tooth by means of a spatula, palate or like tool. This manual technique resulted in the tooth being filled from the outside in. It was noted that this spatula technique of placing such composite resulted in the formation of voids within the finished restoration. This was because the spatula or palate technique of placing such material in a tooth could not satisfactorily pack the paste composite material into the small and difficult to reach areas of the tooth. The placement of such composite material with a palate or spatula also resulted in the entrainment of air and the formation of air bubbles in the composite material as it is being placed. The formation of such voids or air bubbles compromised the strength and durability of the finished restoration. A further difficulty that was encountered by the dentist was that such composite material had a tendency to stick to the palate or spatula, causing the material to be pulled away when the dentist removed the palate or spatula. Also, if a dentist used a metal instrument to place the composite material, there was a tendency of the metallic instrument to react and discolor the composite.

The problems initially encountered by the dentist in placing such composite resins were solved by the development of the syringing technique for the placement of such composite materials. This syringing technique was first disclosed in U.S. Patent 3,581,399 granted June 1, 1971 to Dr. William B. Dragan. The syringing technique and unit dose capsules disclosed in said U.S. Pat. No. 3,581,399 was followed up by other capsule improvements as disclosed in U.S. Pat. Nos. 4,963,093; 4,969,816; 5,083,921; 5,129,825; 5,165,890 and 5,172,807. These known capsule constructions proved satisfactory for placing the composite materials having a paste-like consistency and/or a composite material having a filler content of less than 78% by weight.

Other known capsules from which such paste-like composites could be syringed are disclosed in U.S. Pat. Nos. 4,330,280; 4,384,853; 4,391,590; 4,767,326; 5,100,320; 5,322,440; 5,460,523 and 5,707,234.

Generally, these known capsules are provided with a reservoir portion for containing a predetermined supply of dental material having an internal diameter which is substantially greater than the internal diameter of the discharge orifice. These known capsule constructions have been designed to handle and be used with the then available composites having a paste-like consistency, i.e., a composite resin composition having a filler content of 78% by weight or less. The lower the filler content, the less viscous the material, and the more readily it can be syringed through the relatively small discharge orifice of the known capsule designs.

More recently, the composite dental materials are being formulated with a substantially larger filler content, i.e., more than 78% filled whereby such highly filled or ultra dense composites are rendered "packable" or "condensable" to imitate amalgam in consistency. Such ultra dense or condensable composite materials are particularly suitable for restoring the back or posterior teeth. The particular condensable properties of such ultra dense composite materials makes it difficult to dispense from bulk syringes. The extreme viscous properties of such ultra dense dental composites have also prohibited the placement of such ultra dense composite material by the use of the syringing technique utilizing the known capsule constructions, which the dental profession has virtually universally adopted as the preferred method of delivering a composite material directly into a prepared cavity.

SUMMARY OF THE INVENTION

An object of this invention is to provide a capsule construction particularly suitable for effecting the placement of ultra dense or highly filled composite resin dental restorative materials by means of the syringing technique.

Another object is to provide a capsule construction for dispensing an ultra dense or packable composite resin material directly to a tooth in a manner to minimize any formation of voids.

Another object is to provide a capsule and plug arrangement which is particularly suitable for packaging and dispensing an ultra dense compactable composite resin material.

The foregoing objects and other features and advantages are attained by a capsule construction having a generally cylindrical shaped body portion defining a reservoir for receiving a predetermined amount of ultra dense dental composite resin material. The body portion is provided with a full opening at one end with the other end thereof terminating in a nozzle having a discharge orifice disposed at an angle relative to the central longitudinal axis of the body portion. The body portion defining the reservoir is provided with an internal diameter which is equal to or only slightly larger than the internal diameter of the nozzle and discharge orifice. The internal surface or bore of the body portion is uniform and smooth throughout and is connected in communication with the passageway of the nozzle and free of any obstruction in the transitional area therebetween. The ratio between the internal diameter of the nozzle discharge orifice or opening (d) relative to the internal diameter of the body portion (D) preferably ranges between 1 to 1 to 0.60 to 1. The open end of the body portion is sealed by a displaceable piston which may be spherical, cylindrical and/or a combination thereof so as to be rendered bidirectional. Adjacent the open end, the internal surface of the body portion is provided with one or more longitudinally extending venting grooves to facilitate the venting of any entrapped air upon the insertion of the displaceable piston. A laterally extending collar or flange circumscribes the open end of the body portion and a sealing member is fitted to the nozzle for sealing the discharge orifice.

IN THE DRAWINGS

FIG. 7 is a perspective view of a piston for use with the capsule of FIG. 1.

FIG. 8 is a perspective view of a modified piston construction.

FIG. 9 is a perspective view of another modified piston construction.

FIG. 10 is a perspective view of another modified piston construction.

FIG. 11 is a modified form of the invention.

FIG. 12 is a perspective view of another modified embodiment.

FIG. 13 is a perspective view of still another embodiment.

FIG. 14 is a perspective view of still another embodiment.

DETAIL DESCRIPTION

Figure 1:
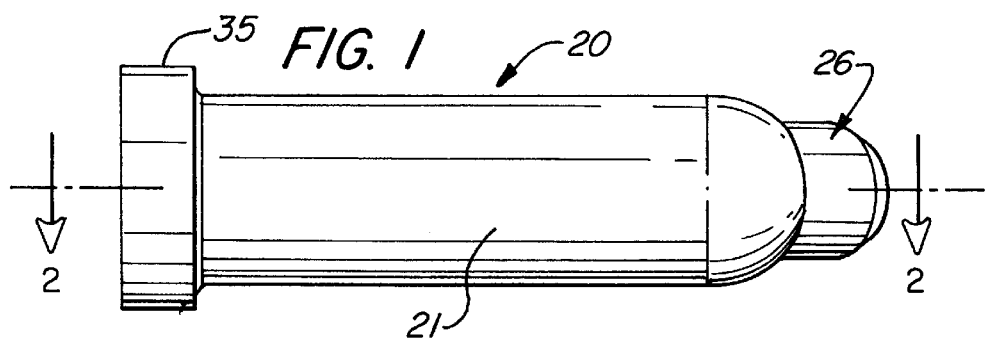
FIG. 1 is a top plan view of a dental capsule embodying the invention.
Figure 2:
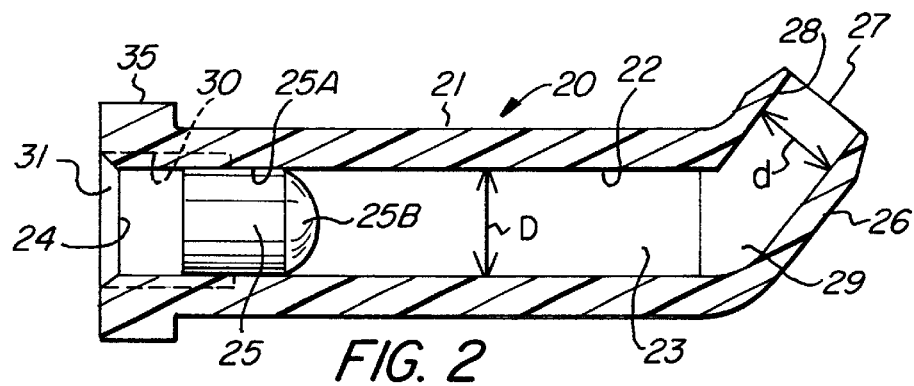
FIG. 2 is a sectional view taken on line 2—2 of FIG.
Figure 3:
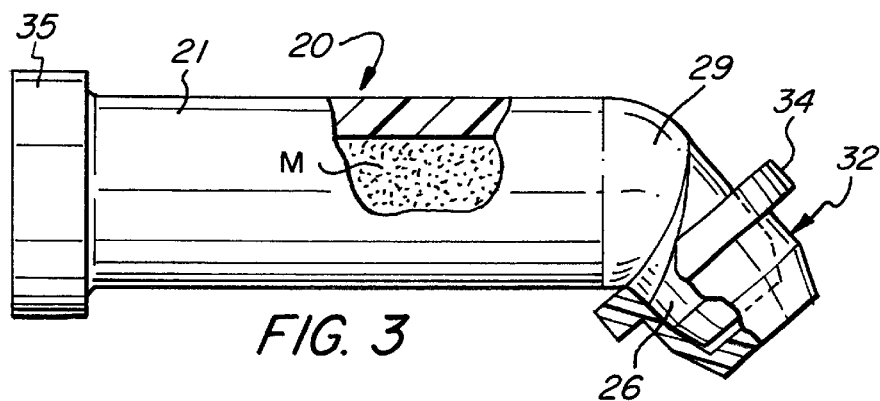
FIG. 3 is a side view of the capsule of FIG. 1 with a sealing cap and having portions broken away.
Figure 4:
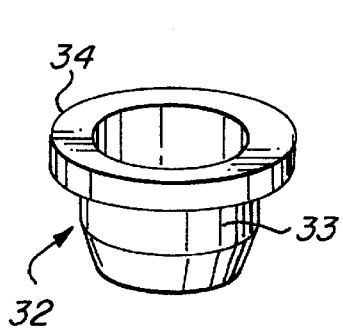
FIG. 4 is a detail perspective view of the sealing cap.
Figure 5:
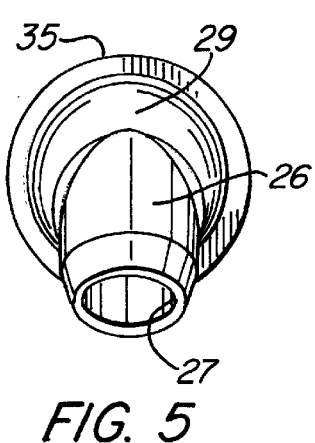
FIG. 5 is a front end view of the capsule of FIG. 1 with the sealing cap removed.
Figure 6:
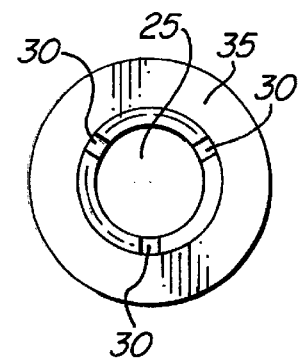
FIG. 6 is a rear or left end view of FIG. 2.

Referring to the drawings, there is illustrated in FIGS. 1 to 3 one form of the invention. As shown, the dental capsule 20 is specially constructed for use with ultra high density dental composite restorative material. Ultra high density dental composite material as used herein is defined as a dental composite restorative resin material having in excess of 78% by weight of a filler material which may comprise barium, aluminum silicate, fumed silica, glass, quartz or other inorganic fillers commonly used by the makers of composite resin dental material. Composite resin material having a filler content in excess of 78% renders the composition "condensable" or "packable" to simulate amalgam, which renders such ultra highly dense composites suitable for restoring the molars or back teeth.

Heretofore, such ultra dense composites could not be placed by utilizing the preferred syringing technique, which is now widely accepted as the preferred method of placing composites in effecting a tooth restoration.

In order to render such ultra dense composites syringeable so as to attain all of the benefits attributed to the syringing technique, the capsule construction 20 is provided with a cylindrical body portion 21 having an internal bore 22 defining a reservoir 23 for containing a predetermined amount of ultra dense composite material M. One end of the capsule body portion 21 is provided with a full open end 24 which is sealed or closed by a displaceable piston 25, as will be herein described. It will be noted that the bore 22 is of a uniform diameter throughout the length of the body portion 21.

Connected to the other end of the body portion 21 is an angularly disposed nozzle 26 terminating in a discharge orifice 27. The passageway 28 formed in the nozzle and terminating at the discharge orifice 27 also has a constant diameter throughout the length thereof. At the bend defined by the intersection of the axis of the nozzle passageway 28 and the axis of the body portion, there is formed a slight transition zone 29. The arrangement is such that the internal walls defining the nozzle passageway 28, the bore 22 of the capsule body 21, and the transition zone 29 therebetween are free of any obstruction so as to permit the uninterrupted flow of the ultra dense material therethrough with a minimum of any resistive forces acting thereon during the extrusion of the ultra dense material M. To achieve this result, the optimal ratio of the internal diameter "D" of the bore 22 relative to that of the internal diameter "d" of the passageway 28 is 1 to 1 or approximately 1 to 1. However, it will be understood that this ratio may vary slightly. For example, if the diameter "D" of bore 22 is 0.150 inches and diameter "d" of the nozzle passageway 28 is equal to 0.125 inches, satisfactory results can still be obtained. Thus, the ratio of relative diameters, i.e. d/D of this example is 0.83, which is slightly less than the optimal ratio of 1 to 1. The lower ratio permits a slight reduction of the internal diameter of the nozzle discharge passageway 28 relative to that of the internal bore 22 to accommodate the placement of the material into a smaller prepared cavity of the tooth to be restored by the syringing technique. An optimum ratio of said diameters d/D may range between 0.60 to 1.

It will be understood that the ultra dense material M placed in capsule 20 can be readily extruded by placing the capsule in any of the known syringe guns, e.g. such as disclosed in U.S. Pat. No. 4,198,756 and those subsequently patented which embody the mechanical advantage of U.S. Pat. No. 4,198,756.

As best seen in FIG. 2, one or more venting grooves 30 may be formed in the internal wall of the body portion 21 adjacent the open end 24. As shown, the venting grooves 30 define a vent means through which any air entrapped within the capsule may be displaced when the piston 25 is inserted to seal the material M therein. With the piston 25 in place, the piston effectively seals off the vent grooves 30 to the outside atmosphere.

Piston 25 is provided with a cylindrical portion 25A having a diameter sized so as to be frictionally received within the bore 22 of the capsule body. The leading end 25B of the piston is curvilinear to complement the slight curvature of the transition zone 29 so that a maximum amount of the material within the reservoir 23 may be extruded.

In the illustrated embodiment, the mouth 31 of opening 24 diverges slightly outwardly, as indicated, to facilitate the insertion of piston 25. It will thus be apparent that as the piston 25 is displaced by the force of the syringe plunger acting on the piston as disclosed in U.S. Pat. No. 4,198,756, the dense material M is expressed as a "rod" through the discharge orifice 27, with a minimum of resistance, other than sliding resistance.

To seal the discharge orifice to prevent any contamination of the material within the capsule and/or to prevent any light from penetrating, in the event the material M is light activated, a sealing cap 32 is provided. In the illustrated embodiment, the sealing cap 32 is provided with a cup shaped body 33 sized to be frictionally retained on the discharge nozzle 26. Circumscribing the opening of the sealing cap 32 is a laterally extending circumscribing flange 34.

It will be understood that in the event the dental material is light activated, the capsule is fabricated of a material that is opaque to the actinic light of the dental material as more particularly set forth in U.S. Pat. No. 5,122,057, which is incorporated herein by reference.

The capsule 20 may also be provided with a laterally extending flange or collar 35 which circumscribes the open end 24.

To minimize any resistance attributed to sliding friction between the ultra dense material M and the internal walls of the capsule, when a force is being applied to the piston 25 to extrude the material out of the capsule, the internal walls or surfaces of the capsule may be lightly coated or lubricated with a material that does not interfere with the chemistry of the composite material.

Preferably, the coating material should comprise a component of the composite composition itself. As the composite material includes as a part thereof a liquid monomer, said liquid monomer may be used to lubricate the internal surfaces of the capsule without adversely effecting the chemistry of the composition. Coating the internal walls of the capsule with the liquid monomer results in (1) minimizing frictional resistance between the material M and the internal walls of the capsule due to sliding friction and (2) minimize any loss of the liquid portion of the composite material as it is being extruded due to the pressure or force being imparted to the material as it is being extruded. It will be understood that the lubricant may also comprise a silicone or Teflon, which may be applied to the inner surfaces of the capsule or be added to the material out of which the capsules may be molded, in which case the lubricating material is integrally molded in the capsule.

FIGS. 8, 9 and 10 illustrate other alternative piston construction which may be utilized in the capsule 20 described. The piston 36 of FIG. 8 comprises a cylindrical body having opposed flat or blunt ends 37, 38. The piston 36 has the advantage of ease of manufacture as the piston 36 can be readily fabricated by forming a rod and thereafter severing such rod into several parts to form the piston 36. Thus, a mold is not essential in forming a piston 36.

FIG. 9 illustrates another modified piston construction. Piston 40 of FIG. 9 includes a central cylindrical body portion 41 having similar or identical spheroidal end portions 42, 43. It will be understood that the opposed end portions 42, 43 may be hemispherical, ellipsoidal or other curvilinear or arcuate shape. The advantage of piston 40 is that it is immaterial which end of the piston 40 is first inserted into the open end of the capsule. Thus, the piston construction of FIGS. 8 and 9 are bi-directional which is important during the assembly and/or filling of the described capsule.

FIG. 10 illustrates a piston 50 which is formed in the shape of a sphere. It will be understood that the diameter of the sphere shaped piston 50 is such that the outer surface of the sphere piston 50 is disposed in sealing relationship to the internal walls of the capsule body, as seen in FIG. 11. The spherical piston 50 has the advantage that when used, it defines a line contact seal with the internal walls of the capsule and minimizes any sliding friction between the piston 50 and the internal walls of the capsule. Also, the piston 50 eliminates any need to orient the piston 50 relative to the capsule during assembly.

FIG. 11 illustrates a modified form of the invention. In this form, the capsule construction 60 is identical to that described with respect to FIGS. 1 to 3. However, in the embodiment of FIG. 11, the nozzle of the capsule 60 is sealed by an end plug 61. The end plug has a stem 62 sized to seal the passageway 63 formed in the nozzle 64 of capsule 60. Connected to the stem 62 is a flange 65 which functions as a stop to limit the insertion distance of the stem 62. With the plug 61 in place as shown in FIG. 11, the orifice opening of the nozzle is tightly sealed. The piston 66 shown in FIG. 11 comprises a spherical piston, hereinbefore described with respect to FIG. 10. In all other respects, the construction and functioning of capsule 60 is similar to that described with respect to capsule 20 of FIGS. 1 and 2.

FIG. 12 is a perspective view of a further modification of the invention. In this form, the capsule 70 has a curvilinear body 71 of a predetermined radius R to define a smooth uninterrupted passageway extending from the open end 72 of the capsule 70 to the discharge orifice 73. In this form of the invention, the passageway or bore 74 has a uniform diameter throughout the length of the body 71. It will be understood that the orifice 73 is sized so as to minimize any resistant forces during extrusion of the ultra dense composite material. In this form of the invention, the spherical piston 50 would be ideal for extruding the material through the nozzle orifice 73. A laterally extending flange or collar 75 circumscribes the opened end 72. Capsule 70 may also be provided with one or more venting grooves 76 of the type hereinbefore described with respect to the embodiment of FIG. 2.

It will be understood that the discharge orifice 73 of capsule 70 may be sealed either by a sealing cap 32 or end plug 61 as previously described with respect to FIGS. 3 and 10.

In this form of the invention, the bore of the capsule body 71 is of uniform or constant diameter D from the open end 72 to the discharge orifice 73 so as to have the optimum ratio of 1 to 1 as hereinbefore described.

In all other respects, the operation or functioning of capsule 70 is similar to that hereinbefore described.

FIG. 13 illustrates another slightly modified embodiment. As shown, the capsule 80 is virtually similar to that of FIGS. 1 to 3 with the exception that the internal diameter D of the capsule cylindrical body portion 81 is equal to diameter D' of the nozzle passageway 82, which terminates at the discharge orifice 83. The nozzle portion 84 is angularly disposed similar to that described with respect to FIGS. 1 to 3. In all other respects, the capsule 80 is similar in structure and function to that described with respect to FIGS. 1 to 3.

FIG. 14 illustrates yet another embodiment. In this embodiment, the capsule 90 has a body portion 91 which defines the reservoir for containing a predetermined amount of the ultra-high density or viscous material. Capsule 90 is provided with a bore having a uniform or constant diameter D therethrough and is open at one end 92. The other end 93 is closed by a sloping or curvilinear end wall 94. In this form of the invention, the discharge orifice 95 is disposed in the wall portion of the capsule body adjacent the end wall 94. Circumscribing the open end 92 is a lateral extending circumscribing flange 96. It will be understood that any of the pistons hereinbefore described may be used to seal the ultra high viscosity material within the capsule 90.

In this form of the invention, the discharge orifice 95 is formed with a diameter "d" which may be equal to or slightly less than diameter D of the bore of capsule 90 so as to define a ratio of d/D ranging between 0.60 to 1.

To seal the discharge orifice 95, capsule 90 is provided with a sealing cap 97 which is frictionally fitted to the closed end 93 of the capsule 90 with sufficient depth to seal the orifice 95. The open end of the seal cap 97 is provided with an outwardly extending flange 98, which provides an edge to facilitate the placement of the sealing cap 97 onto and off the closed end 93 of the capsule 90. In all other respects, the construction and operation of capsule 90 is similar to that hereinbefore described.

From the foregoing, it will be noted that the principle common to each of the described embodiments for rendering ultra dense, compactable or condensable material syringeable so as to prohibit the formation of voids, is that the diameter of the passageway of the nozzles and/or discharge orifice of the described capsules be equal to or relatively close to the diameter of the capsule body portion with no corners or shaped angles disposed in between. In this manner, the ultra dense composite material is caused to be displaced as a "slug" in being forced out of the discharge orifice during an extruding operation, with little or no resistance being imparted thereto. Coating the internal surfaces of the described capsule constructions with a thin film of a lubricant compatible with the ultra dense composite material, functions to further reduce or minimize any sliding friction occurring between the "slug" of material and the internal walls of the capsule during extrusion.

It will be understood that the capsules described herein are preferably made of a suitable plastic material which is compatible with the composition of the ultra dense composite material dispensed thereby. Such plastic materials may be selected from the group consisting of polypropylene, nylon, delrin, and/or like materials such as previously taught in the dental capsule art herein cited.

The pistons may also be formed of similar type plastic materials and/or rubber or synthetic rubber.

While the present invention has been described with respect to a particular embodiment, modifications and variations may be made without departing from the spirit or scope of this invention.

What is claimed is:

1. A dental capsule for dispensing an ultra high viscosity dental composite material directly into a prepared tooth by a syringing technique comprising:
    a capsule body defining a reservoir for containing a predetermined amount of ultra high viscosity dental material,
    said capsule body having an opening at one end and a connected nozzle at the opposite end,
    said nozzle having a passageway terminating at a discharge orifice,
    said capsule body having an internal diameter (D), and said nozzle having an internal diameter (d) whereby the ratio of $d/D$ is in the range of 0.60 to 1,
    a displaceable piston disposed in said body portion and sealing said opening at said one end,
    and including vent means adjacent said opening at said one end.

2. A dental capsule as defined in claim 1 wherein said displaceable piston comprises a sphere disposed in sealing relationship within said capsule body.

3. A dental capsule as defined in claim 1 wherein said piston includes a central cylindrical portion and opposed similar spheriodal end portions connected to said central cylindrical portion.

4. A dental capsule as defined in claim 1 wherein said piston comprises a cylinder shaped member having blunt end portions.

5. A dental capsule as defined in claim 1 wherein said nozzle is disposed at an angle relative to said capsule body portion.

6. A dental capsule as defined in claim 5 and including a transition between said body and said nozzle free of any obstruction.

7. A dental capsule as defined in claim 1 wherein said capsule body and connected nozzle are disposed along a curvilinear axis defined by a common radius.

8. A dental capsule as defined in claim 7 and including a displaceable piston disposed in said capsule body for sealing the material therein, and said piston having the shape of a sphere.

9. A dental capsule as defined in claim 1 wherein said piston is bi-directional.

10. A dental capsule as defined in claim 1 and including means for sealing said discharge orifice.

11. A dental capsule as defined in claim 1 wherein said capsule body is rendered opaque to visible light.

12. A dental capsule as defined in claim 1 wherein said capsule body is rendered opaque to the actinic light of the ultra dense composite material adapted to be dispensed thereby.

13. A unit dose capsule for directly dispensing a dental material directly to a tooth by syringe placement comprising:
    a capsule body having an internal diameter "D" defining a reservoir,
    said capsule body having an opening at one end thereof and a nozzle connected to the other end thereof,
    said nozzle having a passageway connected in communication with said reservoir,
    said passageway terminating at a discharge orifice,
    said passageway and discharge orifice having an internal diameter "d" whereby the ratio of "d"/"D" is in the range of 0.60 to 1,
    said nozzle being angularly disposed relative to the axis of said capsule body,
    a venting groove adjacent said opening,
    a predetermined amount of ultra high density composite resin material disposed in said reservoir,
    a displaceable piston disposed in said capsule body for sealing said opening,
    a laterally outwardly extending flange circumscribing said opening,
    and removable means for sealing said discharge orifice.

14. A dental capsule as defined in claim 13 wherein said displaceable piston is bi-directional.

15. A dental capsule as defined in claim 13 wherein said displaceable piston is spherical.

16. A dental capsule for dispensing an ultra high viscosity dental composite material directly into a prepared tooth by a syringing technique comprising:
    a capsule body defining a reservoir for containing a predetermined amount of ultra high viscosity dental material,
    said capsule body having an opening at one end and a connected nozzle at the opposite end,
    said nozzle having a passageway terminating at a discharge orifice,
    said capsule body having an internal diameter (D),
    and said nozzle having an internal diameter (d) whereby the ratio of $d/D$ is in the range of 0.60 to 1,
    and including a lubricating film coating the internal surfaces of said body and nozzle.

17. A dental capsule as defined in claim 16 wherein said lubricating film comprises a material compatible with the ultra dense composite material adapted to be dispensed by said capsule.

* * * * *